United States Patent [19]

Blank et al.

[11] Patent Number: 4,696,757

[45] Date of Patent: Sep. 29, 1987

[54] STABLE HYDROGEN PEROXIDE GELS

[75] Inventors: Robert G. Blank, Vineland; Dhiraj S. Mody, Hammonton, both of N.J.

[73] Assignee: American Home Products Corporation, New York, N.Y.

[21] Appl. No.: 874,739

[22] Filed: Jun. 16, 1986

[51] Int. Cl.[4] ............ C08K 5/14; C08L 71/02
[52] U.S. Cl. .................... 252/186.29; 252/315.1; 424/53; 424/62; 502/160; 523/105; 524/377
[58] Field of Search ............ 424/62, 53, 78; 524/377, 386; 252/186.29; 502/160; 523/105, 122

[56] References Cited

U.S. PATENT DOCUMENTS

| | | | |
|---|---|---|---|
| 3,639,574 | 2/1972 | Schmolka | 424/62 |
| 4,404,113 | 9/1983 | Peters et al. | 252/71 |
| 4,431,631 | 2/1984 | Clipper et al. | 424/53 |
| 4,528,180 | 7/1985 | Schaeffer et al. | 424/52 |

OTHER PUBLICATIONS

Periogene Publication, Maxell Corp., Hunt Valley, MD.
Affidavit of Robert G. Blank.

*Primary Examiner*—Peter F. Kulkosky
*Attorney, Agent, or Firm*—John W. Routh

[57] ABSTRACT

Aqueous hydrogen peroxide gels possessing enhanced low temperature stability, useful in treating surface cuts and bleaching hair, are prepared employing certain polyoxyethylene polyoxypropylene block copolymers as gelling agents together with glycerine.

2 Claims, No Drawings

STABLE HYDROGEN PEROXIDE GELS

BACKGROUND OF THE INVENTION (a) Field of the Invention

This invention relates to hydrogen peroxide gels stable at low temperatures. More particularly this invention relates to aqueous hydrogen peroxide gels prepared employing certain polyoxyethylene polyoxypropylene block copolymers and glycerine.

(b) Prior Art

Aqueous hydrogen peroxide gels prepared employing polyoxyethylene polyoxypropylene block copolymers are described in United States Pat. No. 3,639,574, herein incorporated by reference in its entirety. The patent describes the preparation of gels by, for example, adding the components at temperatures of 35° F. to 50° F. with stirring to form a solution and then allowing the solution to warm to room temperature whereby a gel is formed. The gels are said to be useful in treating surface cuts and bleaching hair. One disadvantage of these gels is that they liquefy when cooled to temperatures below about 50° F. creating problems in cold weather shipping, storage and use. It has now been found that replacement of some of the water by glycerine in the gel formulation prevents liquefaction at temperatures below about 50° F.

SUMMARY OF THE INVENTION

According to this invention low temperature stable gels of aqueous hydrogen peroxide and polyoxyethylene polyoxypropylene block copolymers are provided by replacement of part of the water by glycerine such that the gel composition contains at least 30% by weight glycerine.

DETAILS OF THE INVENTION

The gels of the present invention comprise, based on a total of 100 parts by weight, (a) from about 5 parts to 20 parts hydrogen peroxide, (b) from about 20 parts to about 60 parts of water, (c) from about 18 parts to about 30 parts of a polyoxyethylene polyoxypropylene block copolymer, and (d) from about 30 parts to about 40 parts of glycerine. The polyoxyethylene polyoxypropylene block copolymer is preferably the grade sold by BASF as Pluronic F-127, or Poloxamer 407, in the form of prills. This grade corresponds to Copolymer P in Table 1 of U.S. Pat. No. 3,639,574.

Typical formulations having low temperature stability according to this invention are described in the following examples.

EXAMPLE 1

The formulation of this example contains the materials shown below on a parts by weight basis and in grams per two kilograms of formulation.

|  | Percent | G/2 kg. |
| --- | --- | --- |
| PLURONIC F-127 BASF Poloxamer 407 (prills) | 20.00 | 400 |
| Glycerine, 96% concentrate | 40.00 | 800 |
| Water, deionized | 25.40 | 508 |
| Hydrogen Peroxide, 35% aqueous solution | 14.30 | 286 |
| Disodium edetate, USP | 0.005 | 1.0 |
| Mint Flavor | 0.25 | 5.0 |
|  | 100.00 | 2000.0 |

The formulation was prepared by first placing the deionized water into a temperature controlled mixing vessel maintained at a temperature of 0° to 5° C. by means of an ice bath. The mixing vessel was a laboratory scale Gifford-Wood homogenizer mixer having rotor and stator blades and vortex and homogenizer operating positions.

The PLURONIC F-127 prills were added slowly with the homo-mixer in the vortex position in about 10 minutes. The homo-mixer was then turned to the homogenizer position and mixing continued for about 20 minutes. The mixture thickened to the extent that the homo-mixer became ineffective. The mixture was then transferred to a Hobart mixer and mixed for one-half hour during which time the mint flavor was added. The mixture was removed from the mixer and allowed to come to room temperature. The pH was 5.95 and the specific gravity was 1.08. The viscosity TD at 4 rpm and 25° C. was 420,000 cps and the viscosity on the third day was 390,000 cps.

EXAMPLE 2

The formulation of this example was changed from that of Example 1 by decreasing the PLURONIC F-127 content from 20% to 17.5% and increasing the water content from 25.4% to 27.9%.

|  | Percent | G/2 kg. |
| --- | --- | --- |
| PLURONIC F-127 BASF Poloxamer 407 (prills) | 17.50 | 350 |
| Glycerine, 96% concentrate | 40.00 | 800 |
| Water, deionized | 27.90 | 558 |
| Hydrogen Peroxide, 35% aqueous solution | 14.30 | 286 |
| Disodium edetate, USP | 0.005 | 1.0 |
| Mint Flavor | 0.25 | 5.0 |
|  | 100.00 | 2000.0 |

The procedure was the same as in Example 1 except that the mixing vessel was not cooled with an ice-bath, the temperature being maintained at about 15° C. using a circulating cold water system. The pH was 5.62, the specific gravity was 1.10. The initial viscosity TD at 40 rpm and 25° C. was 255,000 cp and the viscosity after a day was 250,000.

The formulations of each of Examples 1 and 2 were stored overnight in a refrigerator at 41° F. They were examined the next morning and had remained a gel. Two additional formulations were prepared similar to that of Example 1 except that they contained less glycerine, and more water, i.e. 20 parts by weight 96% glycerine and 25 parts by weight 96% glycerine. These gel formulations were also placed in the refrigerator overnight but when examined the next day they were in liquid phase.

Similarly, formulations similar to that of Example 1 were prepared wherein the 40 parts by weight of glycerine were replaced by sorbitol and propylene glycol respectively. When these gel formulations were placed in the refrigerator overnight, they too were in liquid phase the next day.

Instead of the PLURONIC F-127, Poloxamer 407 employed in the specific examples, other block copolymers can be employed. Suitable block copolymers are of the formula

wherein a is an integer such that the hydrophobe base represented by ($C_3H_6O$) has an average molecular weight of from 2750 to 4000 and b is an integer such that the hydrophile portion represented by ($C_3H_4O$) constitutes from about 45 to 80 weight percent of the copolymer.

PLURONIC F-127 has a hydrophobe base with an average molecular weight of 4000, a hydrophile portion constituting 70 weight percent of the copolymer, and a copolymer average molecular weight of 13,500.

EXAMPLE 3

The formulation of this example was changed from that of Example 2 by increasing the PLURONIC F-127 content from 17.5% to 18.5% and decreasing the water content from 27.9% to 26.9%.

|  | Percent | G/2 kg. |
| --- | --- | --- |
| PLURONIC F-127 BASF Poloxamer 407 (prills) | 18.50 | 370 |
| Glycerine, 96% concentrate | 40.00 | 800 |
| Water, deionized | 26.90 | 538 |
| Hydrogen Peroxide, 35% aqueous solution | 14.30 | 286 |
| Disodium edetate, USP | 0.005 | 1 |
| Mint Flavor | 0.25 | 5.0 |
|  | 100.00 | 2000.0 |

The procedure was the same as that of Example 2 except that the mixing vessel was not maintained at about 15° C. using a circulating cold water system and the temperature in the mixer rose to about 30° C. The pH was then adjusted to 4.1 with citric acid since hydrogen peroxide is more stable at a lower pH. The viscosity after a day was about 110,000 to 115,000 cp. The formulation was stored overnight in the refrigerator at 41° F. and remained a gel the next morning.

EXAMPLE 4

The formulation of this example was changed from that of Example 2 by decreasing the glycerine content from 40% to 30% and increasing the water content from 27.9% to 37.9%.

|  | Percent | G/2 kg. |
| --- | --- | --- |
| PLURONIC F-127 BASF Poloxamer 407 (prills) | 17.50 | 350 |
| Glycerine, 96% concentrate | 30.00 | 600 |
| Water, deionized | 37.90 | 758 |
| Hydrogen Peroxide, 35% aqueous solution | 14.30 | 286 |
| Disodium edetate, USP | 0.005 | 1.0 |
| Mint Flavor | 0.25 | 5.0 |
|  | 100.00 | 2000.0 |

The procedure was otherwise the same as Example 2. The formulation was stored overnight in a refrigerator at 41° F. and had remained a gel when examined the next morning.

Samples of the formulations of Examples 2 and 3 were heated to 98° F. and the gel of Example 2 liquefied but the gel of Example 2 did not. Hence a block copolymer content of at least 18% by weight and a glycerine content of about 30% by weight is necessary for maintaining the formulations of this invention as a gel for the broad range of atmospheric temperatures encountered in summer and winter, i.e. about 35° F. to 105° F.

We claim:
1. A gel stable at temperatures below about 50° F. comprising, based on a total of 100 parts by weight,
    (a) from about 5 parts to about 20 parts of hydrogen peroxide,
    (b) from about 20 parts to about 60 parts of water, and
    (c) from about 18 parts to about 30 parts of a copolymer of the formula

    $HO(C_2H_4O)_b(C_3H_6O)_a(C_2H_4O)_bH$ wherein a is an integer such that the hydrophobe base represented by ($C_3H_6O$) has an average molecular weight of from 2750 to 4000 and b is an integer such that the hydrophile portion represented by ($C_2H_4O$) constitutes from about 45 to 80 weight percent of the copolymer, and
    (d) at least 30 parts of glycerine.
2. The stable gel of claim 1 wherein the copolymer has a hydrophobe base having an average molecular weight of about 4000 and the hydrophile portion constitutes about 70 weight percent of the copolymer.

* * * * *